United States Patent [19]

Tanaka et al.

[11] Patent Number: 4,997,373
[45] Date of Patent: Mar. 5, 1991

[54] ARTIFICIAL TEETH FOR MOLARS

[75] Inventors: Yoshinobu Tanaka, Aichi; Akira Hasegawa, Inuyama; Fujio Yamagishi, Kasugai, all of Japan

[73] Assignee: G-C Toshi Kogyo Corporation, Kasugai, Japan

[21] Appl. No.: 354,229

[22] Filed: May 19, 1989

[30] Foreign Application Priority Data

May 27, 1988 [JP] Japan ................................ 63-128439

[51] Int. Cl.⁵ .............................................. A61C 13/08
[52] U.S. Cl. .................................. 433/204; 433/202.1
[58] Field of Search ............... 433/191, 192, 193, 194, 433/201.1, 202.1, 204, 205, 206, 207, 209, 197, 198

[56] References Cited

U.S. PATENT DOCUMENTS

| | | | |
|---|---|---|---|
| 1,118,703 | 11/1914 | Todd | 433/193 |
| 1,174,886 | 3/1916 | Marx | 433/204 |
| 1,683,614 | 9/1928 | Hallowell | 433/202.1 |
| 1,714,892 | 5/1929 | Robinson | 433/209 X |
| 1,903,730 | 4/1933 | Gillespie | 433/204 |
| 1,986,175 | 1/1935 | Worhol | 433/205 |
| 2,819,525 | 1/1958 | Spiro et al. | 433/204 |
| 3,628,248 | 12/1971 | Kroder | 433/201.1 X |
| 3,958,334 | 5/1976 | Heimansohn | 433/205 X |
| 4,186,486 | 2/1980 | Gordon | 433/201.1 |
| 4,758,162 | 7/1988 | Dobbs | 433/191 X |
| 4,775,319 | 10/1988 | Knapp | 433/223 X |

Primary Examiner—Robert P. Swiatek
Assistant Examiner—Nicholas D. Lucchesi
Attorney, Agent, or Firm—Oblon, Spivak, McClelland, Maier & Neustadt

[57] ABSTRACT

An artificial tooth for molars is of a double structure comprising an occlusal region replaceable by a material which is more durable than a synthetic resin and is selected from the group consisting of a metal, a ceramic, a composite resin and an amalgam, and a bottom region. The present artificial tooth may further include a junction region having a maximum thickness of 0.05 to 3.0 mm, which serves to make a bond between the occlusal and bottom regions of the artificial tooth.

4 Claims, 3 Drawing Sheets

ARTIFICIAL TEETH FOR MOLARS

BACKGROUND OF THE INVENTION

1. Field of the Invention

The present invention relates to a double structure and material of artificial molars designed such that at the point of time when artificial teeth for molars formed of synthetic resins, ceramics or composite materials thereof assumes a occlusal geometry accommodative to various oral functions in the oral cavity of a patient, only the occlusal regions of the artificial teeth are replaced by metals, composite resins, castable ceramics or amalgams of durability with respect to abrasion, and such replacement of the occlusal regions.

2. Description of the Prior Art

Occlusion expressed in terms of the dentition relation of the upper and lower jaws has an appreciable influence upon mastication, face, pronunciation, etc. In particular, the masticatory function of importance to the lengthening of the life span of humans is one of the lower jaw's motions whose upper limit is defined by masticatory relations. In other words, in order to have the masticatory function improved, it is required to establish the occlusal relation in harmony with jaw motions inherent in patients, restricted by the temporomadibular joints and ligaments and reflectively controlled by the mechanisms of nervous and muscular regulation. If that occlusal relation is in disharmony, then fracturing of dents or periodontal tissues or disorders of the temporomadibular joints or muscle will be caused.

In the preparation of protheses, much importance is also attached to the occlusal geometries thereof in harmony with the masticatory motions of patients, like natural teeth. The same is said of plate dentures. That is, the occlusal geometries of artificial teeth applied to the plate dentures directly govern the functions of the completed dentures. Included in artificial teeth are porcelain teeth, resin teeth, metal teeth and so on. Porcelain teeth, which excel in wear resistance, are frequently used in the form of complete dentures, but need an extended period for occlusal equilibration and give rise to not a few failures of the completed denture artificial teeth. It is difficult to use porcelain teeth for partial dentures, since there is an increase in the amount of artificial teeth to be cut off during alignment. As a result, resin teeth are generally used for plate dentures, esp., partial dentures.

In the actual making of dentures, artificial teeth are aligned or milled-in on an articulator serving as a simulator of a patient prepared on the basis of the records of bite taking or jaw motions, while taking into consideration the health conditions of musculi masticatorii, the temporomandibular joints, the alveolar mucosae and so on, the defects of dents, occlusion, root implantation and inclination of residual teeth, and the like. If such a series of operations are properly carried out, the function of the completed plate denture will then be well-balanced in the oral cavity. However, as the resin denture is used in the oral cavity, its occlusal surface is attrited away, so that its initial geometry is fractured within a relatively short period, resulting in an extreme lowering of the denture's masticatory function. In order to cope with this, it has been carried out to replace the occlusal surface by a metal before attrition proceeds to an extreme level. Specifically, the denture is again attached to an articulator with a model, and each artificial tooth is suitably cut off on its occlusal surface, followed by placement of wax. The geometry of wax is patterned or determined by functional milling-in with an antagonistic dentition, and the wax pattern is fitted to a metal casting. This is called a metal occlusal table. However, not until now is any method for preparing occlusal tables with castable ceramics, composite resins or amalgams by such a technique available.

The following problems arise in connection with the method for making metal occlusal tables wherein the occlusal regions of artificial teeth are suitably cut off to receive softened wax, against which a core or antagonist is pressed to obtain functional occlusion.

(1) The optimum functional occlusion obtainable from natural mastication (hereinafter called normal mastication) through food in normal life is not achieved on articulators using softened wax or by pressing techniques in clinics, even though it is possible to obtain a metal occlusal table formed of a durable metal. Hence, serious problems such as "impossible to bite" and "lingering pain" arise.

This is caused for the following three reasons.

(1—1) In order to obtain the optimum functional occlusion, it is required that patients continue normal mastication over one week to one month. However, pressing techniques using softened wax make it impossible for patients to continue normal mastication over one week to one month in view of the thermal, mechanical and chemical properties of the material of the wax, because the wax assumes plasticity at temperatures from the bodily temperature of humans to warm water and cannot stand up to normal mastication in terms of strength.

(1-2) Regardless of how much patients cooperate with dentists, recording of central occlusion is only achieved in a tense atmosphere prevailing in clinics, no matter how occlusal equilibration or tapping with wax is repeated. It is thus nearly impossible to obtain the optimum functional occlusion of normal mastication in a relaxed atmosphere.

(1-3) Manual or automatic milling-in of regions marked by articulating paper as unfit contact with articulators only gives face-to-face contact occlusion without food. This implies that normal mastication cannot actually and precisely be reproduced with the articulators in spite of the fact that they are orginally a simulator of the oral jaws and craniums of humans.

(2) It is impossible for any person to make the metal occlusal tables for a short time with facility, since considerable skill is needed for the method for making the metal occlusal tables wherein the occlusal regions of artificial teeth are suitably cut out to receive softened wax, against which a core or antagonist is pressed to obtain functional occlusion.

(3) According to the method for making the metal occlusal tables wherein the occlusal regions of artificial teeth are suitably cut out to receive softened wax, against which a core or antagonist is pressed to obtain functional occlusion, they are likely to deform at the time of attachment or detachment without a thickened layer of softened wax, because of its low functional strength. This may lead to an increase in the amount of the metal used and, hence, a rise in the cost of the material.

(4) An increase in the amount of the occlusal surfaces of artificial teeth to be cut out attracts much attention to a metallic color, as viewed in the buccal direction, and poses an aesthetic problem in connection with premolar teeth in particular.

SUMMARY OF THE INVENTION

As a result of intensive and extensive studies made to solve the problems mentioned above, it has been found that they can be solved by the development of a double-structure type of artificial teeth for molars, in which only the occlusal regions are castable or replaceable. It is here to be understood that when the occlusal regions are replaced by composite resins or amalgams, the material of such regions need not be castable.

Reference will now be made to actual ways to solve each of these problems.

(1) If the optimum functional occlusion is judged to be impressed and recorded after the normal mastication for one week to one month, only the occlusal regions of the present artificial teeth are then removed. When casing a metal or castable ceramics, it is sprued and then invested and cast in conventional manners. Alternatively, when replacing the occlusal regions by composite resins or amalgams, it is polymerized in a precise counter-die formed of gypsum or an impression material in conventional manners. With the use of the artificial teeth according the present invention, it is possible to obtain an extremely well-balanced, durable metal, castable ceramic, composite resin or amalgam occlusal table for functional occlusion, which cannot be obtained on articulators or by pressing techniques in clinics. Hence, problems such as "impossible to bite" and "lingering pain" do not arise at all.

(1—1) The bottom of the double-structure type of artificial teeth for molars, in which the occlusal regions are castable or replaceable, is formed of synthetic resins, ceramics or composite material thereof. However, the occlusal regions replaceable by a metal or castable ceramics are primarily formed of the same material as that used for synthetic resin artificial teeth or a slightly wearable material, which does not leave behind any trace of residues after being incinerated at temperatures of hundreds of degrees to up to 1000° C. When replacing the material of the occlusal regions by composite resins or amalgams, the occlusal regions may be formed of a composite material of synthetic resins with ceramics, since the amount of incineration residues need not be reduced to zero. Therefore, the occlusal regions are sufficiently resistant to the normal mastication for one week to one month, and is unlikely to deform by the bodily temperature of humans or warm water, unlike wax. The bottom and occlusal regions of artificial teeth are spaced from each other with a retaining projection contained therein, but are temporarily joined to each other at the buccal and lingual junctions so as to avoid their disengagement during one week to one month period of normal mastication. In view of geometry, therefore, the artificial teeth according to the present invention are somewhat swollen at the buccal and lingual sides, when compared with usual artificial teeth. However, no problem arose during a one-month period of normal mastication that is a temporary period. If the optimum functional occlusion is judged to be impressed and recorded after the lapse of a one-week to one-month period of normal mastication, the temporal buccal and lingual junctions are then cut off by a polishing resin point to remove the occlusal regions from the bottom of the present artificial teeth. When replacing them with a metal or castable ceramics, it is sprued and then invested and cast by conventional methods. The thus cast occlusal regions are subjected to sand blasting and final finishing polish by conventional methods, and are in turn bonded to the bottom regions of the present artificial teeth by a dental bonding agent. Alternatively, when replacing them by composite resins or amalgams, it is polymerized and cured in a precise counter-die formed of gypsum or an impression material by conventional methods. The thus obtained artificial teeth having a metal, castable ceramic, composite resin or amalgam occlusal table for functional occlusion provide the most excellent denture ever produced.

(1-2) With the artificial teeth according to the present invention, the occlusal equilibration thereof, which used to be carried out in clinics, can be performed as normal mastication on an out-patient basis. Hence, it is possible to obtain optimum functional occlusion by normal mastication in a more relaxed atmosphere in comparison with a tense state in clinics.

(1-3) The artificial teeth according to the present invention are subjected to occlusal equilibration as normal mastication in the human oral cavity, which means that human oral cavity acts as an articulator. To put it in another way, a complete solution is provided to the problem that even with the articulator, it is impossible to precisely reproduce actual normal mastication, although it originally simulates the palate and cranium of a human.

(2) The double-structure type of the occlusal and bottom regions of the artificial teeth of the present invention are supplied with a number of geometries and color tones similar to that of known conventional artificial teeth. Therefore, it is unnecessary to rely upon such difficult techniques as cutting-off of the occlusal regions and patterning of the occlusal regions by waxing-up. It is thus possible to shorten the length of time for making artificial teeth provided with an occlusal table for functional occlusion.

(3) Since the occlusal regions of the artificial teeth according to the present invention is incomparably superior to wax in terms of mechanical nature, they do not deform at all, when removed for casting. There is thus a reduction in the amount of a metal, when cast, which allows for a reduction in cost.

(4) The occlusal regions of the artificial teeth according to the present invention can be made thinner than those obtained by conventional methods. Therefore, not much attention is attracted to a metallic color as viewed in the buccal direction on account of the metal when the casting has been too thin. No substantial aesthetic problem arises especially with premolars.

In the following discussion, reference will be made to the double structures, principles and materials of the present artificial teeth for molars, which have their occlusal regions castable or replaceable.

BRIEF DESCRIPTION OF THE DRAWINGS

The present invention will now be explained with reference to the accompanying drawings, which are given for the purpose of illustration alone, and in which.

DESCRIPTION OF THE EMBODIMENTS

Figure 1:
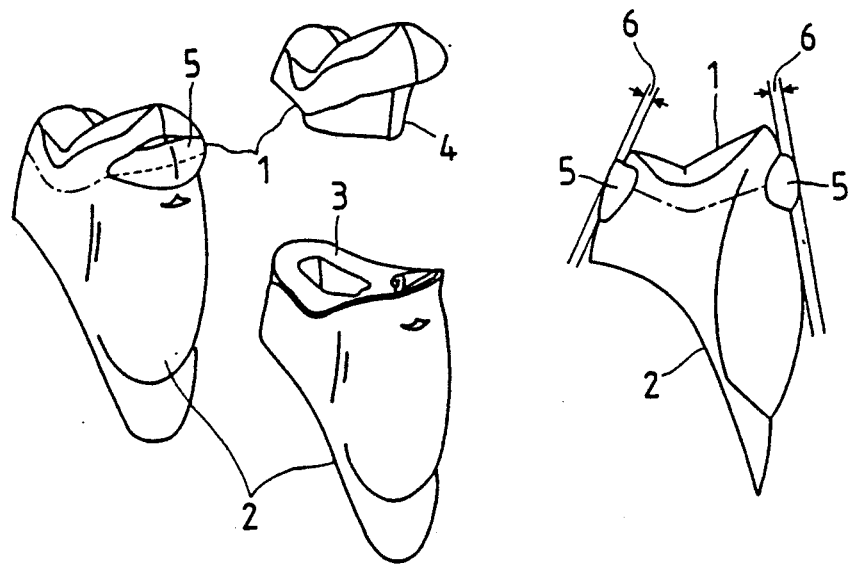
FIGS. 1 to 5 illustrate preferable embodiments of the present invention relating to dens praemolaris primus mandibularis s. inferior, dens molaris primus maxillaris s. inferior, dens paremolaris primus maxillaris s. superior, dens praemolaris secundus maxillaris s. superior and dens molaris primus maxillaris s. superior, respectively.
Figure 2:
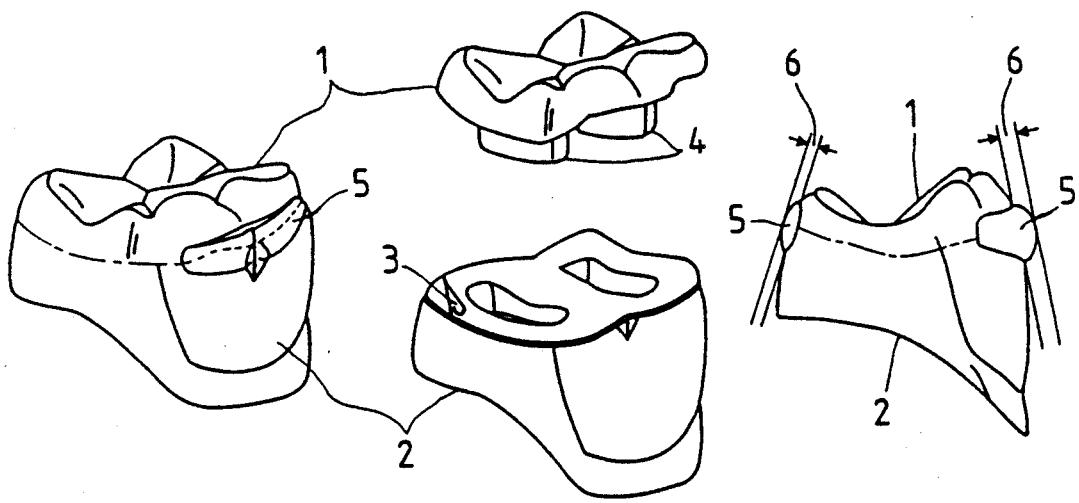
Figure 3:
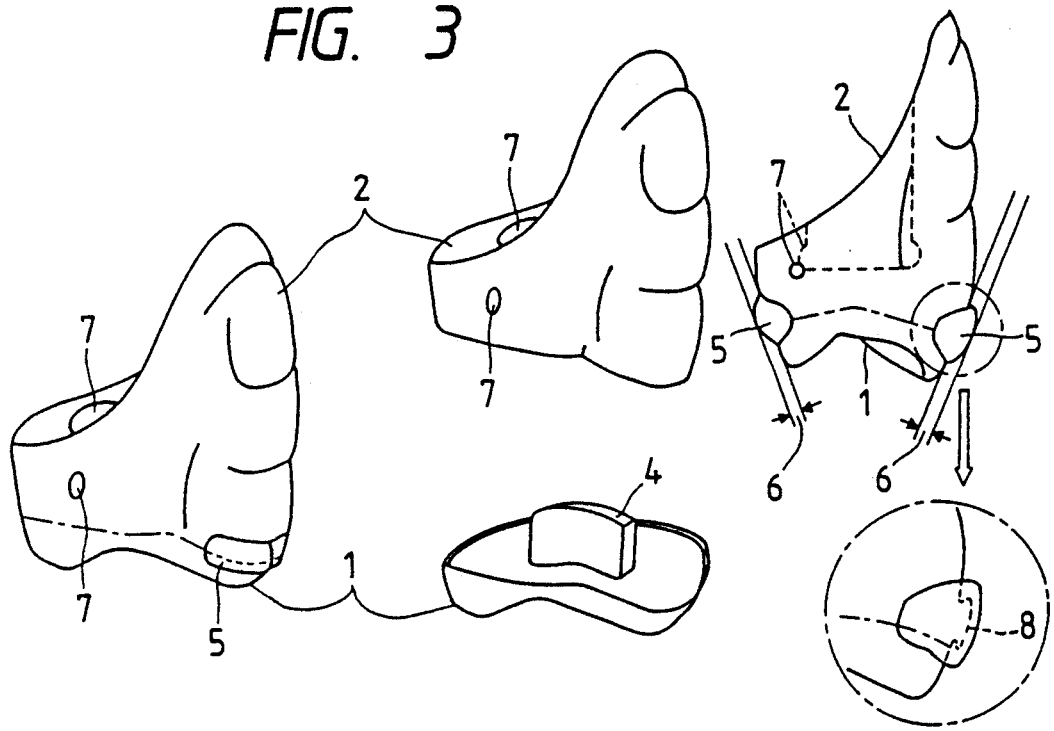
Figure 4:
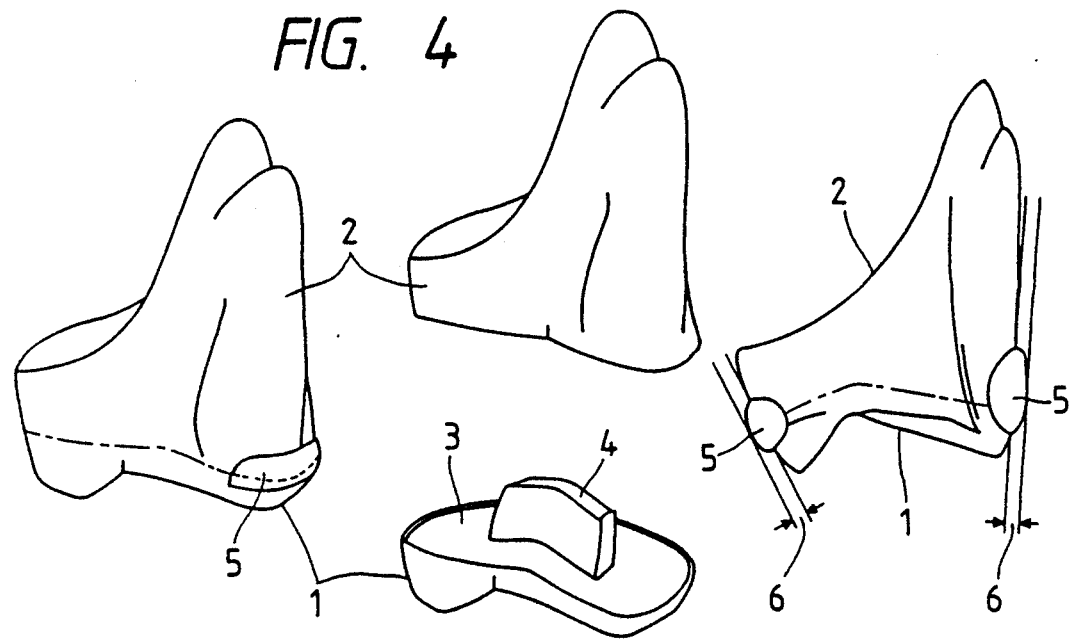
Figure 5:
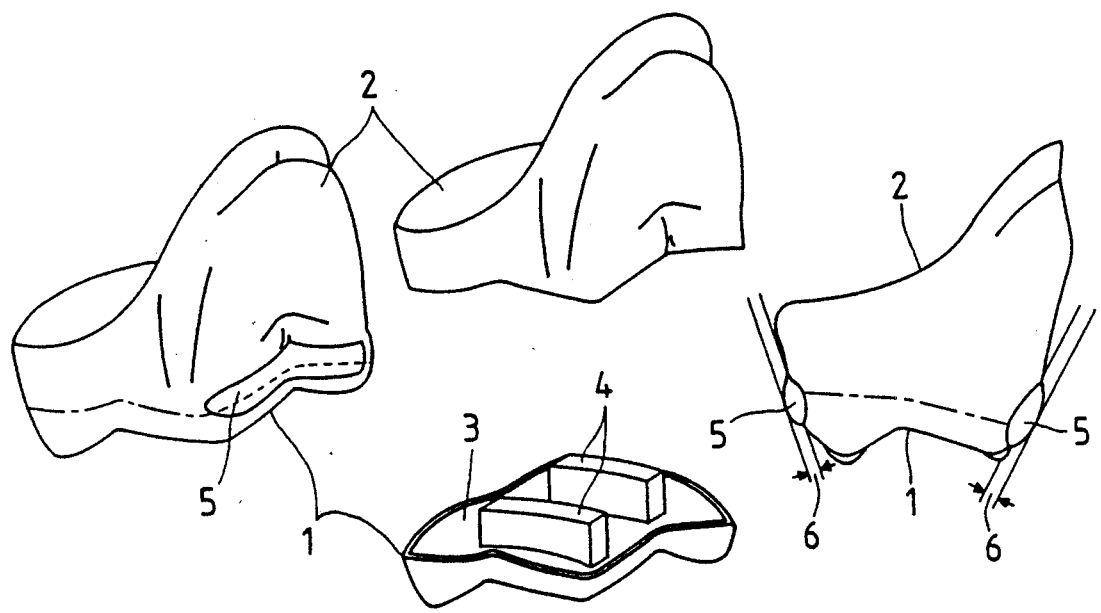

Each of the teeth comprises a castable occlusal region 1 which is removable if the optimum functional occlusion is judged to be impresed and recorded after a one-week to one-month period of normal mastication, (but which need not be castable when replaced by composite resin or amalgam), a bottom region 2 that is formed of a synthetic resin and/or a ceramic material and defines a junction with a plate resin, a separating film or releasing agent 3 for separating the occlusal region 1 from the bottom region 2, a retaining projection 4 designed to engage within the bottom region 2 to hold the occlusal region 1 and the bottom region 2 in place, and an exterior junction region 5 which is separate from and exterior of the occlusal and bottom region and adapted to prevent any disengagement of the occlusal region 1 from the bottom region 2 in the oral cavity, the exterior region 5 having a maximum thickness, as shown at 6. The exterior junction 5 bonds an exterior portion of the occlusal region 1 to an exterior portion of the bottom region 2. The retaining projection 4 is integral with the occlusal region 1, and the bottom region 2 is provided with a recess for receiving it. FIG. 3 illustrates an artificial tooth further including a holding hole 7 for improving the adhesion to a plate resin and a retainer 8 for the occlusal and bottom regions, since that bottom region is formed of a ceramic material.

The double-structure type of artificial (pre)molar teeth having the castable or replaceable occlusal region is subjected on the occlusal region to normal mastication for a period of one week to one month until the optimum functional occlusion is obtained. Two conditions important for the casting of a metal and a castable ceramic material are that the material of the occlusal region is castable and wears away suitably. However, when replaced by a composite resin or an amalgam material, the material of the occlusal region may not be castable. During normal mastication, the occlusal region should be bonded to the bottom region with a bonding force of 5.0 kgf or more, whether it is a premolar or a true molar. However for a bonding force of 5.0 kgf or more, the occlusal region may then be out of place in the oral cavity during the normal mastication. When the occlusal is bonded to the bottom region with such a bonding force, what is of importance is whether they are bonded together over their entire surfaces or through a certain junction. In the present invention, once the occlusal region is completely separated from the bottom region through a separating film or releasing agent, such a suitable bonding force as mentioned above is obtained by the addition of a certain junction. The bonding force is adjusted by the thickness of the junction, but neither on the mesial side nor on the distal side is any junction provided. This is because an alignment of artificial teeth, when provided gives rise to an increase in its lateral diameter, thus presenting an occlusal or aesthetic problem.

It is thus important to position a junction having as large an area as possible and as small a thickness as possible on the buccal and lingual sides so as to avoid geometrical deformation. A strong bonding force is obtained in the present invention, when the occlusal and bottom regions are formed of an identical synthetic or the occlusal region is formed of a synthetic resin, while the bottom region is formed of a composite synthetic resin/ceramics material. Thus, the greater the thickness of the junction, the stronger the bonding force will be. However, since no bonding occurs when the occlusal region is formed of a synthetic resin while the bottom region is made of a ceramic material, mechanical retainer means such as an undercut portion is needed. In the present invention, since the bottom region is first prepared and the occlusal region is molded integrally with the junction through the separating film or releasing agent, the junction region may have a maximum thickness range of 0.05 mm to 3.0 mm, when the bottom region is formed of a synthetic resin or a composite synthetic resin/ceramics material. With the maximum thickness of a junction being of 0.05 mm or less, the occlusal region may possibly be out of place in the oral cavity due to its decreased bonding force to the bottom region, and with the maximum thickness of a junction exceeding 0.3 mm, problems arise in terms of a feeling of incompatibility, or visual appeal. When the bottom region is formed of a ceramic material, the maximum thickness of a junction is preferably a range of 0.05 to 3.0 mm depending upon the geometry of the mechanical retainer, since the occlusal and bottom regions are integrally molded including that retainer. Further, the number of the retaining projections for holding the occlusal and bottom regions in place after the replacement of the occlusal region by a metal, castable ceramics, a composite resin or amalgam may be only one for a premolar and two for a true molar, but is not specifically limited.

The occlusal region is removed and replaced by a durable material in the following manners.

Metal

The retaining projection of the occlusal region removed is sprued with wax—available under the trade name of GC Ready Casting Wax No. 2 (1.5 mm $\phi$)—and a liner—available under the trade name of GC Casting Liner—is lined on the inside of a casting ring, followed by investment with an investment—available under the trade name of GC Crystobalite Micro. Incineration is then carried out by heating at a temperature varying from room temperature to 150° C. over 30 minutes and, then, to 700° C. over 50 minutes in a furnace—available under the trade name of GC Autofurnace—at which the product is maintained for one hour. A metal,—available under the trade name of GC Cast Well MC (a gold content of 12%) is cast with a pressure diecasting machine. After casting, the sprue is cut off by 25-$\mu$m alumina sand blasting to allow for visual observation of the fitness of the occlusal region to the associated bottom region, followed by bonding with a dental bonding agent.

Ceramics

In a similar manner as described in connection with the metal, a sprue is provided and a casting ring is lined with a kaolin ring liner, followed by investment with a phosphate base investment exclusively used for the Dicore systems. Incineration is then carried out by heating at a heating rate of 2° C./min to 250° C. and 950° C., at which temperature the product is maintained for each 30 minutes. The Dicore ingot is heated and maintained at 1370° C. for 6 minutes in a muffle of an exclusive coiling casting machine. Casting is completed for four minutes with a motor-driving type of centrifugal casting machine. After the mold is allowed to cool down to room temperature, the casting is recovered with the removal of investment deposits by 25-$\mu$m alumina sand blasting, followed by ceraming (crystallization). The casting is heated from room temperature to 1075° C. over 100 minutes, at which temperature it is maintained for 6 hours. After cooling, the sprue is cut off to allow for visual observation of the fitness of the occlusal region to the associated bottom region, followed by etching of its inner face with hydrofluoric acid and bonding with a dental bonding agent or cement.

Composite Resin

The occlusal side of the removed occlusal region is invested and cured in anhydrite or super anhydrite, while care is taken so as to avoid the occurrence of undercuts. Afterwards, it is applied thereon with a releasing agent based on sodium alginate and the side of the retaining projection is invested in the same gypsum. After curing, the gypsum is divided to remove the occlusal region and a mixture of equal amounts of GC Microjar Universal—trade name—with a catalyst which is filled to expel air bubbles, followed by the application of a pressure of about 50 kg/cm$^2$. Curing is completed at 23° C. for about 5 minutes, and after-curing is carried out at 90° C. for 1 hour to remove residual monomer. After deburring of the cured product, the occlusal region is bonded to the associated bottom region by means of a dental bonding agent.

Amalgam

In a similar manner as explained above in connection with the composite resin, an alloy, available under the trade name of GC Lumialloy, is filled in a counter-die formed of anhydrite or super anhydride. The alloy is used with mercury at a weight ratio of 1:0.83 in terms of gram, and is kneaded together for 15 seconds with an amalgamator. The kneaded product is packed and filled in the laryngeal region in limited amounts with the use of an instrument. The side of the retaining projection contrary to the laryngeal region is likewise, filled and lightly pressed against a mold for curing. Curing results in a strength of about 60% being reached in 1 hour. Thus, a strong occlusal pressure should not be applied to the occlusal region during curing, even when its bonding to the associated bottom region occurs.

In the present invention, the material of the occlusal region of the artificial tooth has to be a synthetic resin, since it is a requisite for casting that the amount of incineration residues at several 100° C. to 1,000° C. or lower be reduced to zero. However, when replaced by the composite resin or amalgam, use may made of a composite material of synthetic resin and ceramic, since the amount of incineration residues need not be reduced to zero. Used for such synthetic resins are methyl methacrylate, ethyl methacrylate, isopropyl methacrylate, hydroxyethyl methacrylate, tetrahydrofurfuryl methacrylate, glycidyl methacrylate, , 2,2-bis (methacryloxyphenyl) propane, 2,2-[4-(2-hydroxy-3-methacryloxyethoxy-phenyl)]propane, 2,2-bis (4-methacryloxyethoxyphenyl) propane, 2,2-bis (4-methacryopropoxyphenyl) propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate and pentaerythritol tetramethacrylate as well as their related acrylates. These monomers may be used along or mixed or crosslinked in combination of two or more for use. That is, for use, they are all polymerized with an organic peroxide such as benzoyl peroxide, an azo compound such as azobisisobutylonitrile, a pyrimidinetrion derivative such as 1-cyclohexyl-5-ethylpyrimidinetrion or the like. The monomers may be mixed with organic powders and then polymerized for use. Included in such organic powders are those based on polyolefins (such powders as polyethylene and polypropylene), polyacrylates ester (such as polymethylacrylate and polyethylacrylate), polymethacrylate ester (such as polymethylmethacrylate and polyethylmethacrylate), acrylate ester copolymers (such as a copolymer of methyl and ethyl acrylate), methacrylate ester copolymers (such as a copolymer of methyl and ethyl methacrylate), crosslinked type polymethacrylate ester powder (such as polymethylmethacrylate crosslinked with trimethylolpropane trimethacrylate), styrene/butadiene copolymers, styrene, styrene/methyl methacrylate copolymers, acrylonitrile/styrene copolymers, acrylonitrile/styrene butadiene copolymers and nylon, which may be used along or in combination of two or more components.

The bottom region of the artificial tooth according to the present invention may be formed of synthetic resins, ceramics or composite materials of synthetic resins with ceramics. The synthetic resins for that purpose may be the same as described in connection with the materials for the occlusal regions. Included in the ceramics are alumina, magnesia, calcia, zirconia, silica, holsterite, steatite, wollastonite, zircon, mullite, cordierite, spodumene, aluminium titanate, spinel, apatite, boron oxide, silicon nitride, aluminium nitride, boron nitride, titanium nitride, silicon carbide, boron carbide, titanium carbide, tungsten carbide, lithium oxide and the like, which may be used alone or as mixtures, compounds or solid solutions in combination of two or more. The ceramics may be of either crystalline or amorphous structures. In the composite materials of synthetic resins with ceramics, the same synthetic resins as mentioned in connection with the materials for the occlusal regions are reinforced with the ceramics as just mentioned above. Used to this end are a particle-dispersion type of composite materials, short fiber-reinforced composite materials, laminates and interpenetrating network composites. Reinforcements other than the above ceramics may include alumina whisker, beryllium oxide whisker, boron carbide whisker, silicon carbide whisker, boron carbide whisker, various metal whiskers, the so-called organic complex fillers obtained by compacting colloidal silica with a polymer followed by pulverization. It is desired that the ceramics base reinforcements, the various metal whisker, and the organic composite fillers be subjected to coupling treatments so as to increase their adhesion to the synthetic resins. The coupling agents used may include an organofunctional silane coupling agent, a titanate coupling agent, a zircoaluminate coupling agent and so on. The ceramics also may be grafter on the surface to increase its adhesion to the synthetic resins.

The films used to achieve the separation between the occlusal and bottom regions of the artificial tooth in the present invention may be those based on celluose acetate, nitrocellulose, various nylons, polyethylene, polypropylene, Teflon, polyurethane, ionomers, ethylene/vinyl acetate copolymers, polyacrylonitrile, Teflon/ethylene copolymers and so on. The releasing agents used for the same purpose may be those based on Teflon, silicon, nylon coatings and so on. No particular limitation is imposed upon such separating films and releasing agents, provided that they can separate the occlusal regions from the bottom regions.

The retaining projection for achieving well-fitting of the occlusal region of the artificial tooth to the bottom region thereof is formed of the same material as that of the occlusal region, since it is integral with the occlusal region.

The junction region for preventing the occlusal and bottom regions of the artificial tooth in the present invention from being out of place in the oral cavity may be an uncastable ceramics or composite material of synthetic resins with ceramics, since it is cut off prior to casting of the occlusal region. However, preference is given to a castable synthetic resin, since there is a possibility that cutting-off of the junction may be incomplete. Moreover, since the most suitable method for molding the artificial tooth according to the present invention is compression insert molding, the junction region is inevitably formed of the same material as that of the occlusal region.

EXAMPLES

The present invention will be explained with reference to examples and comparison examples. It is to be noted, however, that the present invention is not limited thereto.

Examples 1 to 9

The properties of the artificial teeth according to the present invention are shown in the following table. FIGS. 1 to 5 are exploded sketches illustrating the artificial teeth according to the present invention.

Comparative Examples 1 to 4

These examples are given to define the scope of the present invention. The properties of the comparisons teeth are also shown in the following table.

| | Artificial Tooth | Materials Occlusal Region | Materials Bottom Region | Materials Junction Region | Releasing Materials | Thickness of Junction Region | Bonding Force Between Occlusal and Bottom Regions | Out of Place in Oral Cavity | Replaceable Materials of Occlusal Region | Weight of Replaceable Materials (g) | Mastication and Adaptation Property of Artificial Tooth | Aesthetic View | Hours of Replacement | Feeling Incompatibility during Function Occlusion |
|---|---|---|---|---|---|---|---|---|---|---|---|---|---|---|
| Example 1 | Dens praemolaris primus mandibularis s. inferior | Synthetic resin | Synthetic resin | Synthetic resin | Nylon film | 1.0 mm | 16.2 kgf (3.32) | not occurred | Cast Well 12 manufactured by G-C | 0.37 | Good | Good | Approx. 4 hours | Not felt |
| Example 2 | Dens praemolaris secundus mandibularis s. inferior | Synthetic resin | Synthetic resin | Synthetic resin | Nylon film | 0.1 mm | 5.3 kgf (0.88) | not occurred | Cast Well 12 manufactured by G-C | 0.40 | Good | Good | Approx. 4 hours | Not felt |
| Example 3 | Dens molaris primus mandibularis s. inferior | Synthetic resin | Synthetic resin | Synthetic resin | Nylon film | 2.0 mm | 36.7 kgf (15.5) | not occurred | Cast Well 12 manufactured by G-C | 0.72 | Good | Good | Approx. 4 hours | Not felt |
| Example 4 | Dens molaris secundus mandibularis s. inferior | Synthetic resin | Synthetic resin | Synthetic resin | Nylon film | 1.0 mm | 21.6 kgf (6.33) | not occurred | Castable ceramics* | 0.25 | Good | Good | Approx. 9 hours | Not felt |
| Example 5 | Dens praemolaris primus maxillaris s. superior | Synthetic resin | Ceramic | Synthetic resin | none | 1.0 mm | 19.2 kgf (3.01) | not occurred | Cast Well 12 manufactured by G-C | 0.39 | Good | Good | Approx. 4 hours | Not felt |
| Example 6 | Dens praemolaris secundus maxillaris s. superior | Synthetic resin | Composite material | Synthetic resin | Teflon-base releasing agent | 0.5 mm | 8.1 kgf (1.12) | not occurred | Cast Well 12 manufactured by G-C | 0.39 | Good | Good | Approx. 4 hours | Not felt |
| Example 7 | Dens moraris primus maxillaris s. superior | Synthetic resin | Synthetic resin | Synthetic resin | Silicon-base releasing agent | 2.5 mm | 46.3 kgf (19.9) | not occurred | Cast Well 12 manufactured by G-C | 0.70 | Good | Good | Approx. 4 hours | Not felt |
| Example 8 | Dens moraris secundus maxillaris s. superior | Composite material | Synthetic resin | Composite material | Polyethylene film | 1.0 mm | 22.6 kgf (4.02) | not occurred | Microjar manufactured by G-C | 0.17 | Good | Good | Approx. 3 hours | Not felt |
| Example 9 | Dens praemolaris primus mandibularis s. inferior | Composite material | Synthetic resin | Composite material | Nylon film | 1.0 mm | 14.1 kgf (6.31) | not occurred | Lumialloy manufactured by G-C | 0.51 | Good | Good | Approx. 2 hours | Not felt |
| Comparative Example 1 | Dnes praemolaris primus mandibularis s. inferior | wax | Synthetic resin | none | none | — | — | — | Cast Well 12 manufactured by G-C | 2.10 | Not good | Not good | Approx. 2 days | — |
| Comparative Example 2 | Dnes praemolaris primus mandibularis s. inferior | Synthetic resin | Synthetic resin | Synthetic resin | Nylon film | 0.02 mm | 3.1 kgf (0.18) | occurred | Unable to cast | — | — | — | — | Unable to occlude |
| Comparative Example 3 | Dens molaris primus mandibularis s. inferior | Synthetic resin | Synthetic resin | Synthetic resin | Nylon film | 3.50 mm | 38.6 kgf (13.3) | not occurred | Cast Well 12 manufactured by G-C | 0.73 | Good | Good | Approx. 4 hours | Felt |
| Comparative Example 4 | Dnes molaris secundus mandibularis s. inferior | Synthetic resin | Synthetic resin | Synthetic resin | none | 0 mm | 78.3 kgf (19.6) | not occurred | Unable to cast | — | — | — | — | Not felt |

( ) standard deviation
*Dicor system manufactured by Dentsply

The artificial teeth shown in Examples 1 to 4 are prepared for dens praemolaris primus mandibullaris s. inferior, dens praemolaris secundus mandibularis s. inferior, dens molaris primus mandibularis s. inferior and dens molaris secundus moadibullaris s. inferior, respectively. The occlusal, bottom and junction regions of each tooth are all formed of a synthetic resin, and the separating material is formed of a nylon film. In Example 1, the junction region had a thickness of 1.0 mm, and the occlusal region was bonded to the bottom region with a bonding force of 16.2 kg. In Example 2, the junction region had a decreased thickness, and in Example 3, the junction region had an increased thickness. The thinner the junction region, the smaller the bonding force for making a bond between the occlusal and bottom regions, whereas the thicker the junction region, the larger the bonding force for forming a bond between the occlusal and bottom regions, although such a value is largely dependent upon the type of artificial teeth. However, no problems arise during use, provided that the thickness of the junction regions is in the range as defined in the appended claims. In Examples 1 to 3, the occlusal regions were replaced by Cast Well 12 manufactured by G-C, and in Example 4, the Dicor system (castable ceramics) manufactured by Dentsply was cast. In Example 5, the bottom region is formed of a ceramic material, and is not essentially bonded to a occlusal region formed of a synthetic resin. Therefore, a retainer is needed between the junction and bottom regions, although no separating material is needed. Although no critical limitation is placed on the geometry of that retainer, it has to be provided in its bottom with a projection so as to prevent the material of the junction region from remaining in the bottom region during cutting-off carried out after functional occlusion (see FIG. 3). In Examples 6 and 7, the separating materials are formed of a releasing agent based on Teflon and a releasing agent based on silicon, respectively. In Example 6, the bottom region is formed of a composite synthetic resin/ceramics material. In Examples 5, 6 and 7, the occlusal regions are bonded to the bottom regions with different bonding forces, since the occlusal regions and artificial teeth are different in thickness and size. However, the occlusal regions could be replaced by Cast Well 12 manufactured by G-C without being out of place in the oral cavity, since their thickness was in the range as defined in the appended claims. In Example 8, the occlusal region can be replaced by a composite resin, but cannot by substituted by a metal or castable ceramics, since it is formed of a composite synthetic resin/ceramics material. In the replacement of the occlusal region after functional occlusion, it is replaced by Microjar manufactured by G-C with the use of an impression material or gypsum. In Example 9, the occlusal region is replaced by Lumialloy manufactured by G-C in the same manner as mentioned in connection with the composite resin. In these examples, the length of time required for replacement is about 4 hours for the metal, about 9 hours for the castable ceramics, about 3 hours for the composite resin and about 2 hours for the amalgam. No problems arise at all in terms of the mastication, fitness and aesthetic nature of the dentures and the malfunction thereof during functional occlusion.

In Comparative Example 1, an artificial tooth is obtained for dens praemolaris primus mandibularis s. inferior by the pressing technique using softened wax. The occlusal region is formed by the wax and the bottom region, of a synthetic resin. Neither junction region nor separating material is needed because of the different technique applied. According to this method, a considerable thickness should be added to the wax region so as to prevent its deformation during attachment or detachment. Therefore, since the amount of a metal replaced is much larger in comparison with in Examples 1 to 3 and 5 to 7, the cost increases considerably when noble metals such as gold alloys are used. Since it is not subjected to functional occlusion, the mastication and fitness of the denture are inferior and an aesthetic problem arises due to an increased amount of the metal. Moreover, the length of time required to replace it by other durable materials by casting is about 2 days, which are much longer than that required in the examples. Obtained in Comparative Examples 2 and 3 are artificial teeth for dens praemolaris secundus mandibularis s. inferior and dens molaris primus mandibularis s. inferior, respectively, wherein the occlusal, bottom and junction regions are all formed of a synthetic resin and the separating materials are formed of a nylon film. In Comparative Example 2, the thickness of the junction region is smaller than the lower limit as defined in the appended claims. The occlusal region is bonded to the bottom region with a bonding force so small that the occlusal region is out of place in the oral cavity and so cannot be replaced by other durable material by casting. In Comparative Example 3, the thickness of the junction region exceeds the upper limit as defined in the appended claims. The occlusal region is bonded to the bottom region with a bonding force so sufficient that it can be replaced by other durable material. However, a feeling of incompatibility is given to the patient during functional occlusion in the oral cavity, so that the occlusal region cannot stand up to temporal wearing for one week to one-month. In Comparative Example 4, an artificial tooth is obtained for dens molaris secundus mandibularis s. inferior. The occlusal and bottom regions are both formed of a synthetic resin without using any separating material. In spite of the fact that the thickness of the junction region is zero, the occlusal region is bonded to the bottom region so that the occlusal region may not largely be out of place. However, such an occlusal region cannot be replaced by other durable material.

With the artificial teeth for molars according to the present invention, the following effects are achievable owing to their double structure wherein the occlusal regions can be cast with metals or castable ceramics or replaced by composite resins or amalgams.

(1) In order to obtain the optimum functional occlusion of artificial teeth, it is desired that only their occlusal regions be replaced by durable metals, castable ceramics, composite resins or amalgams after natural mastication occurring through food in normal life, the so-called normal mastication. Such a demand is satisfied by the present artificial teeth for molars which are of the double structure wherein the occlusal regions are castable or replaceable. That is, the optimum functional occlusion is judged to be impressed and recorded after the lapse of one week to a one month period of the normal mastication, the occlusal region of the present artificial tooth is then removed from the bottom region. When it is cast by metals or castable ceramics, investment and casting are then carried out in conventional manners after the provision of a sprue. When it is replaced by composite resins or amalgams, on the other hand, polymerization is carried out in conventional manners after a counter-die has been formed with gypsum or impression materials. With the use of the artificial teeth according to the present invention, it is possible to obtain an extremely well-balanced, durable metal, castable ceramic, composite resin or amalgam occlusal table for functional occlusion, which cannot be obtained on articulators or by pressing techniques in clinics using softened wax. Hence, such problems characterized as "impossible to bite" and "lingering pain" do not arise at all.

(2) The double-structure type of the occlusal region castable or replaceable artificial teeth of the present invention are supplied with the number of geometries and color tones similar to that of known conventional artificial teeth. Therefore, it is unnecessary to rely upon such difficult techniques as cutting-off of the occlusal regions and patterning of the occlusal regions by waxing-up. It is thus possible to shorten the length of time for making artificial teeth provided with an occlusal table for functional occlusion.

(3) Since the occlusal regions of the artificial teeth according to the present invention is incomparably superior to wax in terms of mechanical property, they do not deform at all, when removed for casting. There is thus a reduction in the amount of a metal, when cast, which allows the cost to go down.

(4) The occlusal regions of the artificial teeth according to the present invention can be thinner than those obtained by conventional methods. Therefore, no much attention is attracted to a metallic color as viewed in the buccal direction due to the metal after cast being thin.

No substantial aesthetic problem arises especially, with premolars.

What is claimed is:

1. An artificial two-piece tooth for molars, which comprises:
   an occlusal region which includes a material which is more durable than a synthetic resin and which is selected from the group consisting of a metal, a ceramic, a composite resin and an amalgam;
   a bottom region; and
   an exterior junction region which is separate from and exterior of said occlusal and bottom regions for bonding an exterior portion of said occlusal region to an exterior portion of said bottom region on buccal and lingual sides of said occlusal region.

2. An artificial tooth as claimed in claim 1, wherein said exterior junction region has a maximum thickness of 0.05 to 3.0 mm.

3. An artificial tooth as claimed in claim 1, wherein said occlusal region includes a retaining projection on a back side portion thereof and said bottom region includes a recess which corresponds with and receives said retaining projection on a side portion opposite said occlusal region.

4. An artificial tooth as claimed in claim 1, wherein said bottom region is formed of a material selected from the group consisting of a synthetic resin, a ceramic or a composite synthetic resin/ceramic material.

* * * * *